United States Patent
Casey

(10) Patent No.: US 8,623,749 B2
(45) Date of Patent: Jan. 7, 2014

(54) REDUCTION OF STORED CHARGE IN THE BASE REGION OF A BIPOLAR TRANSISTOR TO IMPROVE SWITCHING SPEED

(75) Inventor: David Neil Casey, Ramsbottom (GB)

(73) Assignee: Diodes Incorporated, Plano, TX (US)

(*) Notice: Subject to any disclaimer, the term of this patent is extended or adjusted under 35 U.S.C. 154(b) by 0 days.

(21) Appl. No.: 13/330,340

(22) Filed: Dec. 19, 2011

(65) Prior Publication Data

US 2012/0322219 A1 Dec. 20, 2012

Related U.S. Application Data

(60) Provisional application No. 61/424,956, filed on Dec. 20, 2010.

(51) Int. Cl.
*H01L 21/22* (2006.01)
*H01L 21/38* (2006.01)
*H01L 21/331* (2006.01)
*H01L 29/66* (2006.01)

(52) U.S. Cl.
USPC ............ 438/555; 438/369; 438/542; 438/554; 257/197; 257/592

(58) Field of Classification Search
USPC ......... 438/170, 189, 204, 236, 309, 325, 327, 438/369, 375, 377, 542, 549, 554–556
See application file for complete search history.

(56) References Cited

U.S. PATENT DOCUMENTS

| | | | | |
|---|---|---|---|---|
| 3,477,886 A | * | 11/1969 | Ehlenberger | 438/546 |
| 3,491,434 A | * | 1/1970 | Cunningham et al. | 438/375 |
| 3,623,925 A | * | 11/1971 | Jenkins et al. | 438/570 |
| 3,759,761 A | * | 9/1973 | Takki et al. | 438/310 |
| 3,938,243 A | * | 2/1976 | Rosvold | 438/571 |
| 4,149,906 A | * | 4/1979 | De La Moneda | 438/325 |
| 4,446,611 A | * | 5/1984 | Bergeron et al. | 438/375 |
| 5,496,746 A | * | 3/1996 | Matthews | 438/350 |
| 5,744,855 A | | 4/1998 | Maki | |
| 5,893,759 A | | 4/1999 | Ikeda | |
| 5,981,349 A | * | 11/1999 | Hebert | 438/381 |
| 7,208,785 B2 | * | 4/2007 | Wu | 257/280 |
| 2003/0222277 A1 | | 12/2003 | Fujii | |

OTHER PUBLICATIONS

Tang et al. "Design Considerations of High-Performance Narrow-Emitter Bipolar Transistors", IEEE Electron Device Letters vol. EDL-8, No. 4 Apr. 1987, pp. 174-175.*
International Search Report from International Patent Application No. PCT/IB2011/003278 mailed May 22, 2012.

* cited by examiner

*Primary Examiner* — Mary Wilczewski
*Assistant Examiner* — Erik T Peterson

(57) ABSTRACT

In one embodiment, a method includes forming a base region for a transistor using a base mask and forming a contact region to the base region. The contact region is formed in an area that is at least partially outside of the base mask. The method then forms an emitter region in a diffused base region. The base region diffuses outwardly to be formed under the contact region.

4 Claims, 5 Drawing Sheets

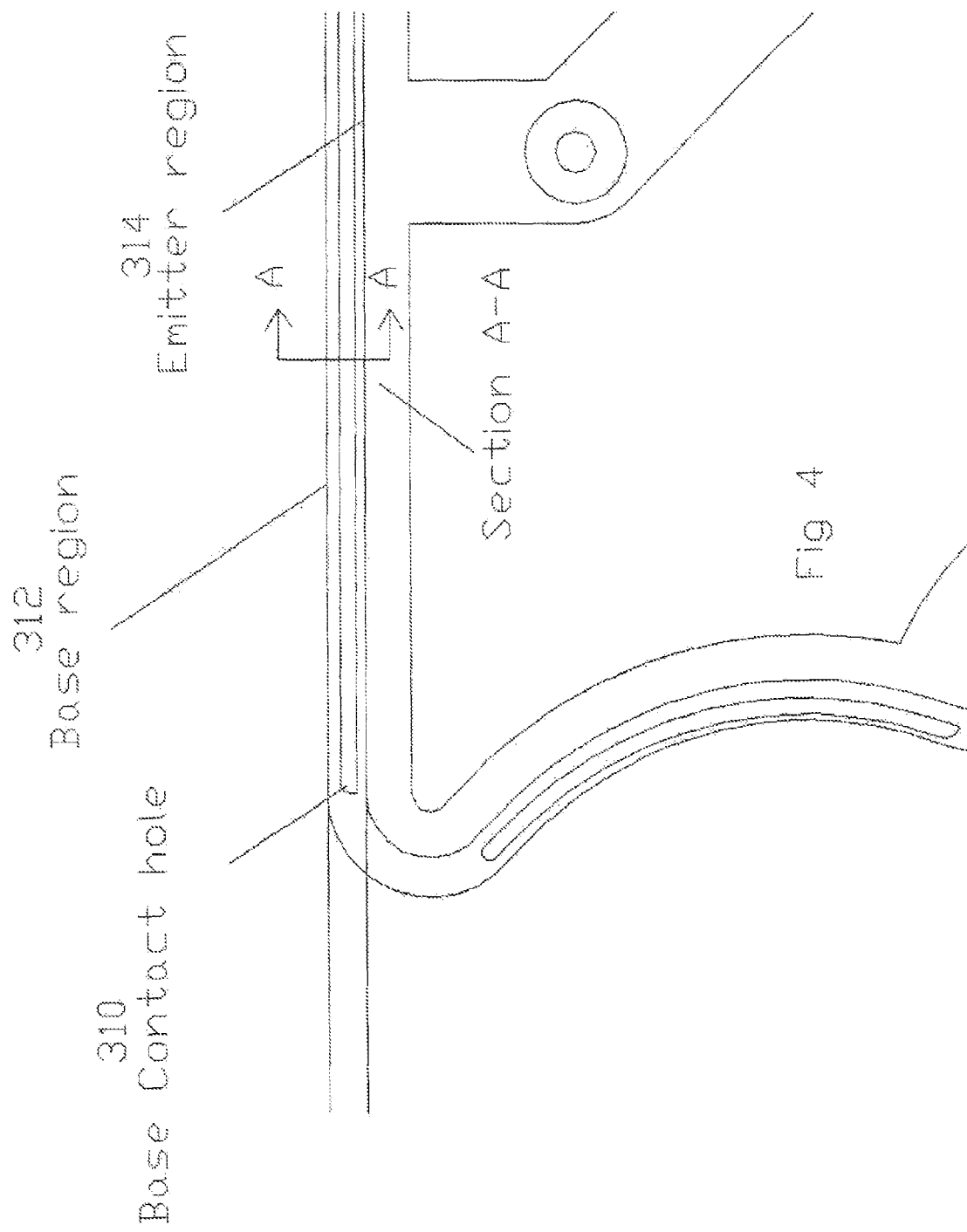

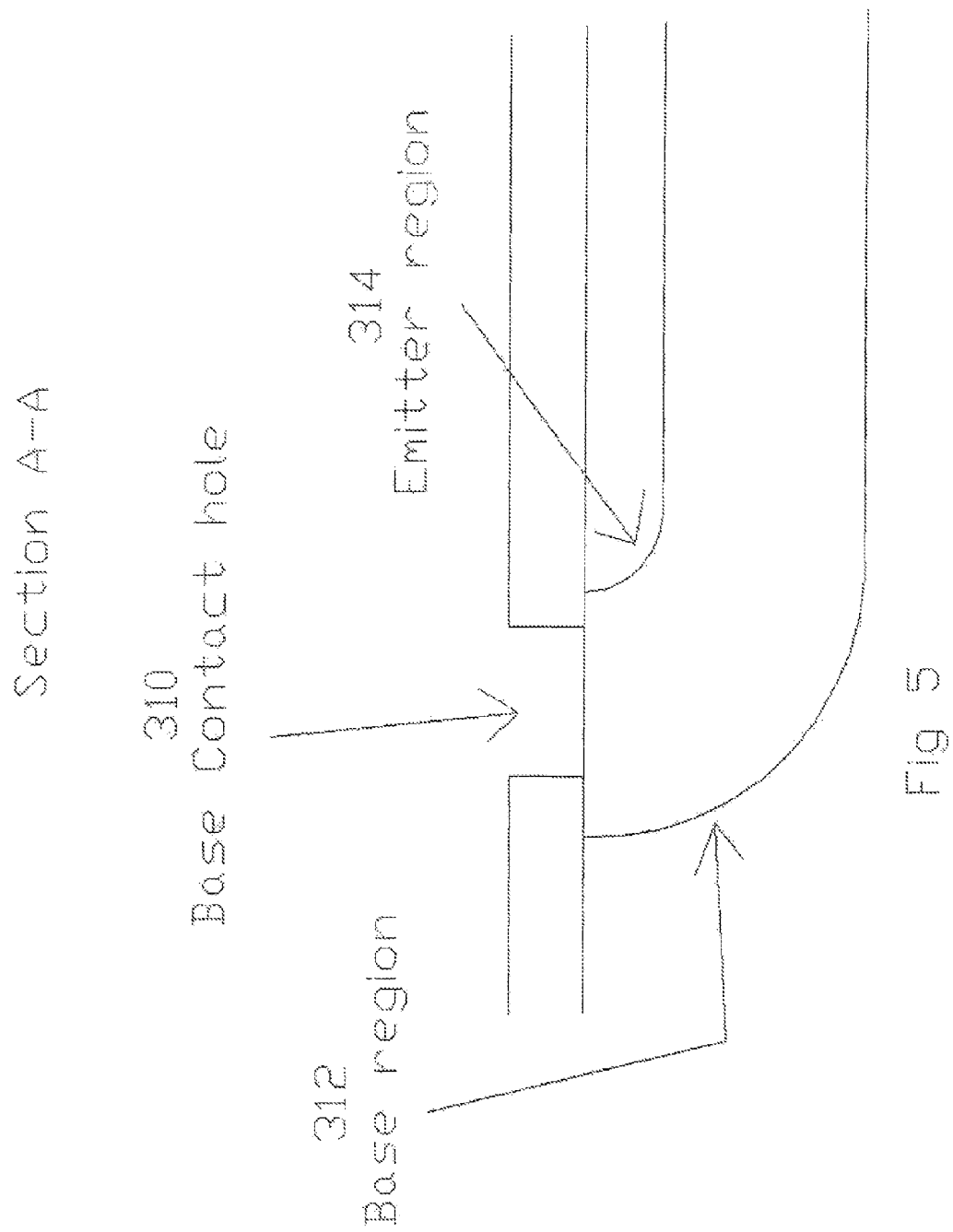

FIG. 5 shows a cross-section A-A from FIG. 3 according to one embodiment.

REDUCTION OF STORED CHARGE IN THE BASE REGION OF A BIPOLAR TRANSISTOR TO IMPROVE SWITCHING SPEED

CROSS REFERENCE TO RELATED APPLICATIONS

The present application claims priority to U.S. Provisional App. No. 61/424,956 for "Darlington with Intermediate Base Contact" filed Dec. 20, 2010, the contents of which is incorporated herein by reference in their entirety.

BACKGROUND

Particular embodiments generally relate to Darlington transistor configurations.

FIG. 1 shows a traditional layout 100. A base contact mask 102 is placed within a base mask outer edge 104. Emitter mask outer edge 106 is placed within a certain distance from base contact mask 102. The emitter needs to be a certain distance from a base contact. The contact is placed in the outer regions of a base diffusion within the outer base region as defined by base mask outer edge 106. However, during the subsequent processing, the outer base edge moves significantly and is then well outside of the region into which the contact is placed. This region contains no useful features such as an emitter diffusion nor even the contacts themselves. This "empty" volume does however store base charge as well as contribute to collector base capacitance. The problem is that in order to switch from an "ON" state to an "OFF state the drive circuit to a transistor has first to remove this stored charge. Thus the presence of this unnecessary volume adds unnecessary stored charge, which slightly increases the switching time. The added capacitance also has a degrading influence but to a lesser extent.

SUMMARY

In one embodiment, a method includes forming a base region for a transistor using a base mask and forming a contact region to the base region. The contact region is formed in an area that is at least partially outside of the base mask. The method then forms an emitter region in a diffused base region. The base region diffuses outwardly to be formed under the contact region.

In another embodiment, a method includes: placing a base mask for a base region for a transistor; placing a contact mask for a contact region to the base region in an area that is at least partially outside of an edge of the base mask; and placing an emitter mask for an emitter region a defined distance away from the contact mask, wherein the base region diffuses outwardly to be formed under the contact region during processing.

The following detailed description and accompanying drawings provide a better understanding of the nature and advantages of the present invention.

BRIEF DESCRIPTION OF THE DRAWINGS

FIG. 4 depicts an example of a layout after processing according to one embodiment.

FIG. 5 shows a cross-section A-A from FIG. 3 according to one embodiment.

DETAILED DESCRIPTION

Described herein are techniques for a layout in which base contacts are placed outside a base region. In the following description, for purposes of explanation, numerous examples and specific details are set forth in order to provide a thorough understanding of embodiments of the present invention. Particular embodiments as defined by the claims may include some or all of the features in these examples alone or in combination with other features described below, and may further include modifications and equivalents of the features and concepts described herein.

Figure 1:
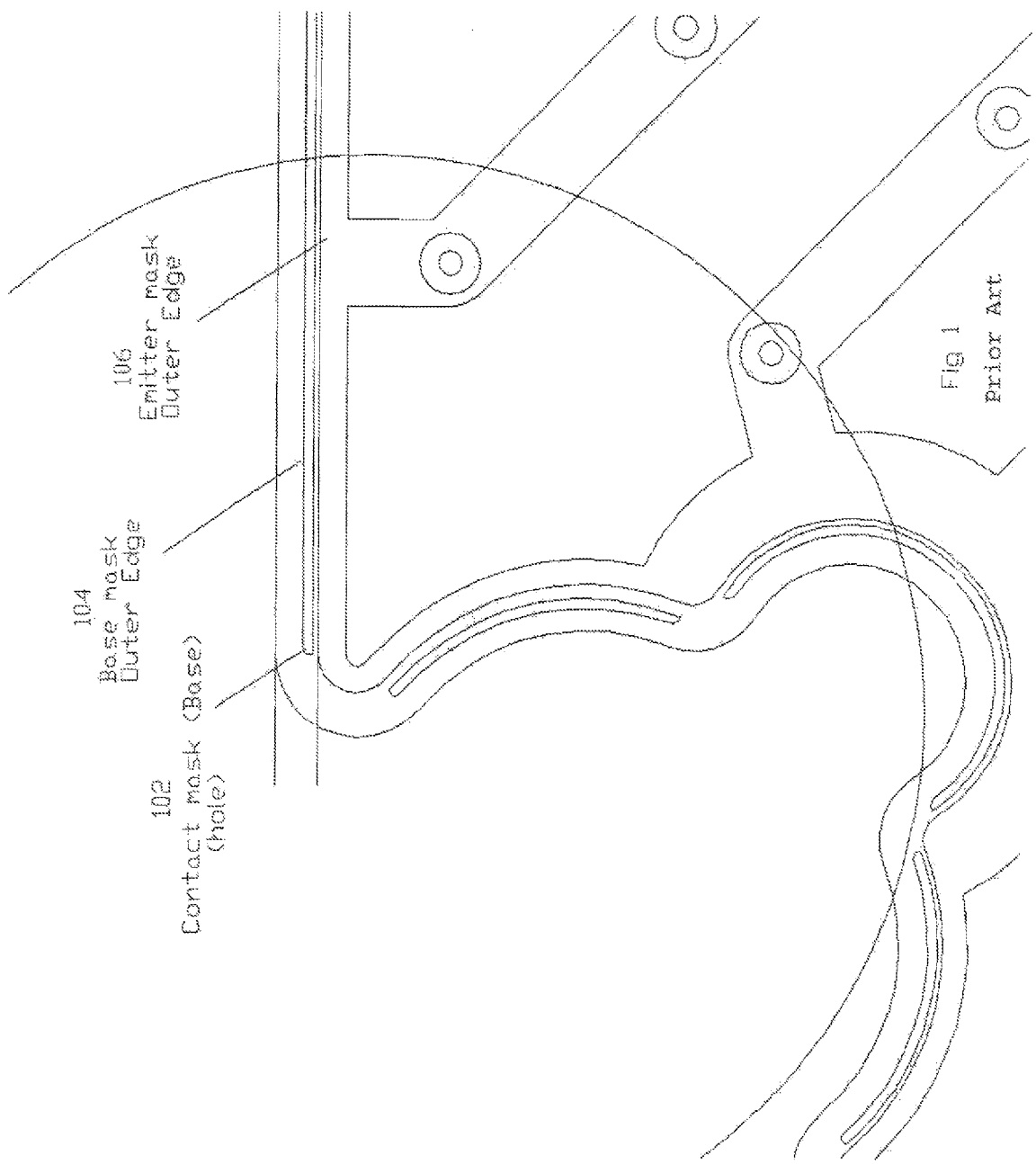
FIG. 1 shows a traditional layout.
Figure 2:
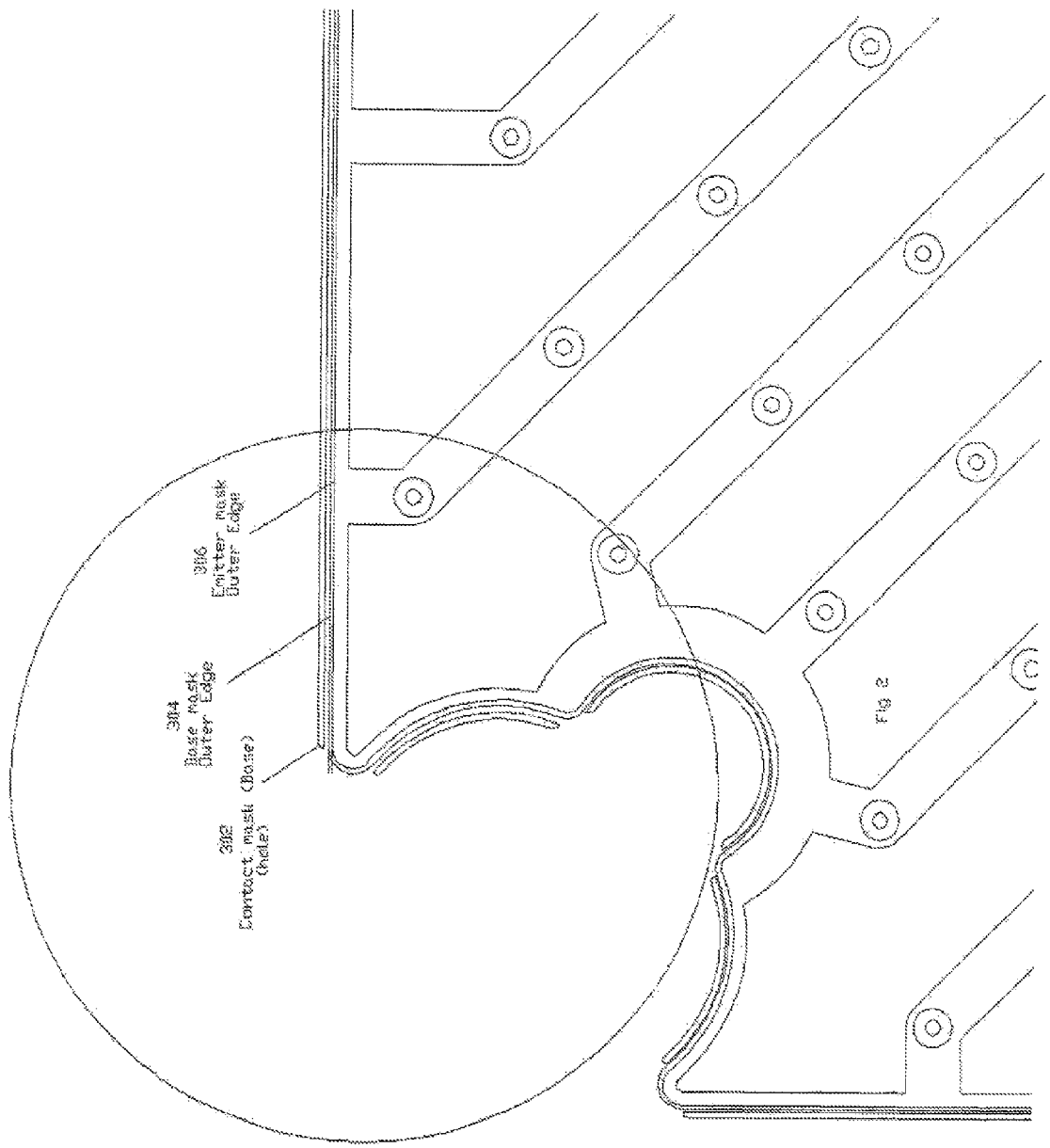
FIGS. 2 and 3 depict an example of a layout in which base contacts are placed outside a base region according to one embodiment.
Figure 3:
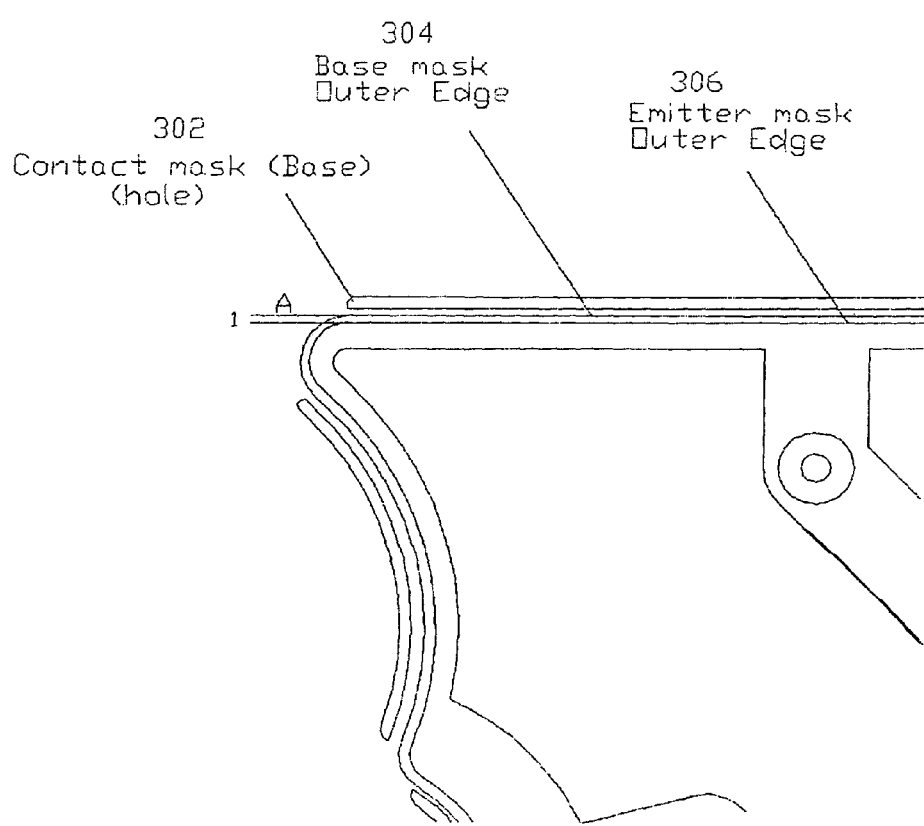

FIGS. 2 and 3 depict an example of a layout in which base contacts are placed outside a base region according to one embodiment. FIG. 3 is a zoomed in version of FIG. 2. The layout may be for a transistor, which may include a bipolar junction transistor (e.g., PNP or NPN) or a metal-oxide-semiconductor field-effect transistor (MOM-ET). The discussion will describe a BJT design. The base region may be defined by a base mask. Base contacts may be placed outside the defined base region as defined by the base contact mask. For example, the outer contacts between the top face base metallization and the underlying silicon base regions may lie outside the base mask region. During processing, the base region diffuses outwardly to be formed under the contact region. This produces a reduction in the base volume that does not contain an emitter diffusion. This improves switching performance by reducing base stored charge, in a way other than reducing base capacitance although base capacitance is also reduced. The base volume that contains emitter does not accumulate stored base charge.

The switching performance of a transistor may be dependent upon charge stored in the base region of the transistor. The stored charge can be reduced by removing any base regions not actually occupied by emitter regions or contacts or regions needed to support electric fields. Particular embodiments leverage the sideways diffusion by placing contacts completely or partially outside a defined base region and into a sideways diffused region of the base region. This permits extension of the emitter outwards by the same amount that the contacts move outwards, which fills the base regions that had previously been occupied by the base contacts. This may reduce the emitter to base distance, such as by 75%. In one example, the base to emitter distance on the surface reduces from 4 μm to 1 μm.

For example, referring to FIGS. 2 and 3, a base contact mask 302 is found outside of a base mask outer edge shown at 304. Also, an emitter mask outer edge 306 may be placed in the base region. The distance in which emitter mask outer edge 306 can be placed to the base mask edge 304 is reduced. An emitter may be moved closer to the base edge because the emitter needs to be a certain distance from the contact. If the contact is moved outside of the base mask edge, then the emitter may be moved closer to the base mask edge 304.

The contacts may or may not be doped with base type dopant after the base has been diffused and prior to deposition of a metal layer. This has the advantage of improving the contact between the metal and the base. This may be a different process for an NPN transistor, but a person of skill in the art will appreciate how to perform the process based on the disclosure and teaching herein.

The switching speed is improved by reducing the base volume that does not contain the emitter. The switching performance is dependent upon charge stored within this unoccupied base region and by reducing this area volume, (the time taken to dissipate the reduced quantity of stored charge is reduced correspondingly).

FIG. 4 depicts an example of a layout after processing according to one embodiment. A base contact hole 310 is shown that has not moved after processing. A base region 312 has diffused outward and is in the region of base contact hole 310. An emitter edge 314 is also shown and is included in base region 312. The amount of emitter diffusion included in base region 312 is increased because emitter region 312 is moved outward due to having base contact hole 310 moved outward.

FIG. 5 shows a cross-section A-A from FIG. 3 according to one embodiment. Base region 312 has diffused outward and is under base contact hole 310. Base region 312 has moved under base contact hole 310 even though contact mask 302 was outside of base mask outer edge 304. Emitter region 314 is also included in base region 312. Accordingly, particular embodiments have leveraged the outer diffusion of base region 312 to move base contact hole 310 outward allowing more area of base region 312 to be diffused by emitter region 314.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The above description illustrates various embodiments of the present invention along with examples of how aspects of the present invention may be implemented. The above examples and embodiments should not be deemed to be the only embodiments, and are presented to illustrate the flexibility and advantages of the present invention as defined by the following claims. Based on the above disclosure and the following claims, other arrangements, embodiments, implementations and equivalents may be employed without departing from the scope of the invention as defined by the claims.

What is claimed is:

1. A method comprising:
    forming a base region for a transistor using a base mask;
    forming a contact hole to the base region completely outside the base mask window; and
    where the base region diffusing outwardly to underlap the contact hole.

2. The method of claim 1, wherein the base region diffuses outwardly in the area at least partially outside of the base mask window.

3. The method of claim 1, wherein an emitter region is placed a distance away from the contact hole, wherein the distance is a defined threshold.

4. The method of claim 1, wherein an emitter mask is placed a distance away from the contact hole, wherein the distance is a defined threshold.

* * * * *